United States Patent [19]

David et al.

[11] Patent Number: 4,486,530

[45] Date of Patent: * Dec. 4, 1984

[54] IMMUNOMETRIC ASSAYS USING MONOCLONAL ANTIBODIES

[75] Inventors: Gary S. David, La Jolla; Howard E. Greene, Carlsbad, both of Calif.

[73] Assignee: Hybritech Incorporated, San Diego, Calif.

[*] Notice: The portion of the term of this patent subsequent to Mar. 8, 2000 has been disclaimed.

[21] Appl. No.: 323,498

[22] Filed: Jun. 24, 1981

Related U.S. Application Data

[63] Continuation-in-part of Ser. No. 175,133, Aug. 4, 1980, Pat. No. 4,376,110.

[51] Int. Cl.³ .................. G01N 33/54; G01N 33/56
[52] U.S. Cl. .................. 435/7; 436/519; 436/523; 436/527; 436/529; 436/534; 436/537; 436/548; 436/800
[58] Field of Search .................. 23/230 B; 424/12; 435/7; 436/519, 523, 527, 529, 534, 537, 548, 800

[56] References Cited

U.S. PATENT DOCUMENTS

| 3,654,090 | 4/1972 | Schuurs | 435/7 |
|---|---|---|---|
| 3,791,932 | 2/1974 | Schuurs | 435/7 |
| 3,867,517 | 2/1975 | Ling | 23/230 B X |
| 3,996,345 | 12/1976 | Ullman et al. | 424/12 |
| 4,016,043 | 4/1977 | Schuurs | 435/7 |
| 4,098,876 | 7/1978 | Piasio | 424/12 X |
| 4,174,384 | 11/1979 | Ullman | 23/230 B X |
| 4,220,450 | 9/1980 | Maggio | 436/537 |
| 4,233,402 | 11/1980 | Maggio | 436/537 X |
| 4,244,940 | 1/1981 | Jeong et al. | 424/1 |
| 4,261,968 | 4/1981 | Ullman | 436/537 X |
| 4,308,026 | 12/1981 | Mochida | 436/523 X |

FOREIGN PATENT DOCUMENTS 7525004 3/1976 France.
2019562 10/1979 United Kingdom.

OTHER PUBLICATIONS

A. C. Cuello et al., Proc. Natl. Acad. Sci., U.S.A., vol. 76(7), 3532-3536, (Jul. 1979).
"Chemical Abstracts", 92, 481 (1980) entry No. 92:74134t.
"Chemical Abstracts", 94, 115 (1981) entry No. 94:203334a.
F. Buchegger et al., "Protides Biol. Fluids", 1980, 511-515.
Strecker et al., "Chemiker Zeitung", 103, 53 (1979).
M. Uotila et al., I, Molecular Immunology, 17(6), 791-794 (Jun. 1980).
M. Uotila et al., II, Journal of Immunological Methods, 42(1), 11-15 (1981).

Primary Examiner—Sidney Marantz
Attorney, Agent, or Firm—William L. Respess

[57] ABSTRACT

"Two-site" or "sandwich" immunometric assay techniques for determination of the presence and/or concentration of antigenic substances in fluids using monoclonal antibodies are described and compared to conventional assays using polyclonal antibodies. Also described are inhibition assays using complexes of antigens with a monoclonal antibody.

33 Claims, 2 Drawing Figures

IMMUNOMETRIC ASSAYS USING MONOCLONAL ANTIBODIES

CROSS-REFERENCE TO RELATED APPLICATIONS

This application is a continuation-in-part of co-pending application Ser. No. 175,133, filed Aug. 4, 1980, now U.S. Pat. No. 4,376,110, the disclosure of which is incorporated by reference.

FIELD OF THE INVENTION

This invention relates to methods for detecting and/or determining the concentration of antigenic substances in fluids such as serum. In another aspect it relates to immunometric and inhibition assay techniques. In yet another aspect it relates to monoclonal antibodies.

BACKGROUND

The determination of the presence or concentration of antigenic substances, for example, those associated with a wide variety of physiological disorders, in serum or other body fluids relies increasingly upon immunoassay techniques. These techniques are based upon formation of a complex between the antigenic substance being assayed and an antibody or antibodies in which one or the other member of the complex may be labelled, for example, by a radioactive element such as $^{125}I$, which permits its detection and/or quantitative analysis after separation of the complexed labelled antigen or antibody from uncomplexed labelled antigen or antibody.

In the case of a competition immunoassay technique, the antigenic substance in a sample of fluid being tested for its presence competes with a known quantity of labelled antigen for a limited quantity of antibody binding sites. Thus, the amount of labelled antigen bound to the antibody is inversely proportional to the amount of antigen in the sample. By contrast, immunometric assays employ a labelled antibody. In such an assay, the amount of labelled antibody associated with the complex is proportional to the amount of antigenic substance in the fluid sample.

Immunometric assays have been found to be particularly well suited for the detection of polyvalent antigens, i.e., antigenic substances that are able to complex with two or more antibodies at the same time. Such assays typically employ a quantity of unlabelled antibody bound to a solid support that is insoluble in the fluid being tested and a quantity of soluble antibody bearing a label such as a radioactive isotope that permits detection and/or a quantitative estimate of the amount of the ternary complex formed between solid phase antibody, antigen, and labelled antibody.

In immunometric assays known to the prior art, typically "forward" assays, in which the antibody bound to the solid phase is first contacted with the sample being tested to extract the antigen from the sample by formation of a binary solid phase antibody: antigen complex, are employed. After a suitable incubation period, the solid support is washed to remove the residue of the fluid sample, including unreacted antigen, if any, and then contacted with a solution containing a known quantity of labelled antibody.

After a second incubation period to permit the labelled antibody to complex with the antigen bound to the solid support through the unlabelled antibody, the solid support is washed a second time to remove the unreacted labelled antibody. In a simple "yes/no" assay to determine whether the antigen is present in the sample being tested, the washed solid support is tested to detect the presence of labelled antibody, for example, by measuring emitted radiation if the label is a radioactive element. The amount of labelled antibody detected is compared to that for a negative control sample known to be free of the antigen. Detection of labelled antibody in amounts substantially above the background levels indicated by the negative control is interpreted to indicate the presence of the suspect antigen. Quantitative determinations can be made by comparing the measure of labelled antibody with that obtained for calibrated samples containing known quantities of the antigen.

This kind of assay is frequently referred to as a "two-site" or "sandwich" assay since the antigen has two antibodies bonded to its surface at different locations. This and related techniques are described by Wide at pp. 199-206 of "Radioimmunoassay Methods," Edited by Kirkham and Hunter, E. & S. Livingstone, Edinburgh, 1970. An assay based on this technique for the detection of the antigen associated with serum hepatitis using an $^{125}I$ labelled antibody is described in U.S. Pat. No. 3,867,517.

Despite their great utility, the prior art immunometric assays have been recognized to be slow procedures, in part because two washing steps are required and because lengthy incubation periods are required to approach equilibrium, i.e., the point at which the amount of complex formed does not change with increasing time.

To eliminate at least one of the washing steps associated with this procedure, so-called "simultaneous" and "reverse" assays have been proposed. A simultaneous assay involves a single incubation step as the antibody bound to the solid support and the labelled antibody are both added to the sample being tested at the same time. After the incubation is completed, the solid support is washed to remove the residue of fluid sample and uncomplexed labelled antibody. The presence of labelled antibody associated with the solid support is then determined as it would be in a conventional "forward" sandwich assay.

A reverse assay involves the stepwise addition first of a solution of labelled antibody to the fluid sample followed by the addition of unlabelled antibody bound to a solid support after a suitable incubation period. After a second incubation, the solid phase is washed in conventional fashion to free it of the residue of the sample being tested and the solution of unreacted labelled antibody. The determination of labelled antibody associated with the solid support is then determined as in the simultaneous and forward assays.

Both the simultaneous and reverse assay techniques require a sufficient excess amount of solid phase antibody to bind most or all of the antigen present to avoid a high dose hook effect where artificially negative or low quantitation of antigen is observed at extremely high concentration of antigen. For this reason, the forward assay has been the approach preferred by the prior art. That is because large amounts of highly purified, active antibody specific to the antigen of interest for preparing a solid phase with sufficient antigen binding capacity is difficult to obtain from the "polyclonal" antibodies used in prior art processes. When an immunogenic substance is introduced into a living body, the body's immune system reacts by generating antibodies to every site on the immunogen it recognizes. A large immunogenic protein molecule may have dozens of sites and a foreign cell may have hundreds. Thus, while each antibody producing cell produces antibody specific for a single antigenic site the immune system has generated a specie of specific antibody producing cells for each immunogenic site recognized. In addition, the body has produced relatively large quantities of antibodies to antigens other than the one of interest such that most of the antibody in the polyclonal mixture is not specific for the antigen of interest. Accordingly, the antibodies used in prior immunometric assays are necessarily "polyclonal" in nature since the antibodies are derived from antisera raised in a conventional manner in animals and their purification is difficult. Methods for affinity purifying such antibodies have generally been time consuming and resulted in low yields and loss of high affinity antibodies.

When employing conventional polyclonal antibody mixtures in the reverse and simultaneous assays, the formation of a "sandwich" comprising the antigen complexed by two or more labelled antibodies which complex with the antigen at different sites is possible. These complexes could remain soluble in the sample being tested, be removed by subsequent washing steps, and not "counted" when the solid phase is analyzed for solid phase bound labelled antibody. If this happens to a significant extent, sensitivity of the assay is reduced and erroneous results may arise. However, if the unlabelled bound antibody is added to the sample first as in the forward sandwich assay, steric considerations prevent formation of a sandwich comprising the antigen complexed to two or more unlabelled antibodies where labelled antibody is excluded from also binding to the antigen. Accordingly, the antigen is free to react with a labelled antibody molecule. Nevertheless, it has been proposed to use a simultaneous assay for human thyroid stimulating hormone (HTSH) by employing a large excess of the unlabelled antibody bound to a solid phase to minimize formation of a soluble complex by soluble labelled antibodies. See Jeong et al., "Comparison of Radioimmunoassay (RIA) with a Unique, Single-Incubation Two-Site Immunoradiometric Assay (IRMA) as Applied to the Determination of Human Thyroid Stimulating Hormone (HTSH)," Bio-Rad Laboratories, 1979.

A variation of a simultaneous assay is described in U.S. Pat. No. 4,174,384. In that assay, separate portions of Anti-IgG (Human) are labelled, respectively, with a fluorescing chromophore (fluorescein) and a chromophore (rhodamine) which absorbs light emitted by the fluorescein. Both antibodies, in a soluble form, are contacted with a sample containing human IgG. Reaction of the Anti-IgG with the IgG may bring the two chromophores close enough together, i.e., within 100 angstroms or less, that the emission of light by the fluorescing chromophore is absorbed (quenched) by the other. The percentage of maximum fluorescence for the sample is determined and used as a measure of the amount of IgG in the sample.

It has also been proposed to use a reverse assay for HTSH, hepatitis associated antigen (HAA) and carcinoembryonic antigen (CEA) by employing a quantity of labelled antibody sufficient to assure a labelled antibody: antigen complex but insufficient to form a "sandwich" of all the antigen present in a sample. See U.S. Pat. No. 4,098,876.

Since all three of the procedures known to the prior art use a polyclonal mixture of antibodies, the potential for cross-reaction with other materials in serum or other fluid than the antigen for which the test is intended is increased. The occurrence of cross-reactivity with other antigens also reduces the sensitivity of the test for the suspect antigen and increases the prospect of a "false-positive" assay. Furthermore, the use of polyclonal antibodies in a simultaneous or reverse assay requires a careful consideration of the amount of labelled antibody used relative to the amount of solid phase antibody and/or antigen present. In the case of using fluorescence quenching, sensitivity is reduced because the minimum spacing between the fluorescing chromophore and the quenching chromophore is not assured when polyclonal antibodies are employed.

In view of these shortcomings, the limitations to the immunometric procedures known to the prior art are readily apparent. The conventional forward assay is time consuming; the simultaneous and reverse assays are accomplished with fewer steps but require large quantities of solid phase specific antibody and are not well suited to determination of small concentrations of antigen since formation of a sandwich of the antigen with a multiple number of labelled antibody molecules competes with formation of the sandwich comprising bound antibody:antigen:labelled antibody or, in the case of using fluorescence quenching, the formation of a sandwich without pairing of a fluorescent chromophore with a quenching chromophore is possible; and all are subject to misinterpretation of false-positives due to the polyclonal nature of the antibody.

Accordingly, one object of the present invention is to provide an improved process for the immunometric assay for antigenic substances.

More specifically, an object of the present invention is to provide more rapid immunometric assay techniques.

Another object of the present invention is to provide more sensitive immunometric assay techniques.

Yet another object of the present invention is to provide improved "simultaneous" and "reverse" immunometric assays.

A further object of the invention is to provide improved inhibition assays.

The manner in which these and other objects are realized by the present invention will be apparent from the summary and detailed description set forth below.

SUMMARY OF THE INVENTION

According to the present invention, the polyclonal antibodies used in an immunometric assay, for example, as the unlabelled antibody bound to a solid support and the antibody used as the soluble labelled antibody or, in the case of assays relying upon fluorescence quenching, the antibodies carrying a fluorescing or quenching chromophore are replaced by at least one and usually two or more different monoclonal antibodies, i.e., each antibody specific to a single antigenic site and separately produced by clones derived from unique cell lines. In a preferred embodiment of the invention, the monoclonal antibody used as the antibody bound to a solid support is the product of a different cell line than is the monoclonal antibody used for the labelled antibody and the two monoclonal antibodies are selected to bind the antigenic substance at sites remote from each other so as to not interfere with the other's binding to the antigen. In the case of fluorescence quenching, the two antibodies are also usually the products of different cell lines and are selected so as to not interfere with the other's binding yet bring the two chromophores close enough together to permit quenching of fluorescence, i.e., usually to within about 100 angstroms. The advantages of the present invention, particularly in simultaneous and reverse assays, over prior art methods will become clear after consideration of the accompanying drawings and the following detailed description of the invention.

Also, according to the present invention, monoclonal antibodies are employed in inhibition assays. In such assays, a known quantity of an antigen and monoclonal antibody is contacted with a sample suspected of containing an antigen corresponding to the known antigen added with the monoclonal antibody. The extent to which inhibition of the complex between the antibody and antigen occurs because a complex comprising the monoclonal antibody and antigen from the sample is formed is a measure of the presence and/or amount of antigen in the sample assayed. In a preferred embodiment, the antibody and antigen are bound, respectively, to one of the members of a pair of fluorescing and quenching chromophores. Inhibition of the formation of a complex between the labelled antigen and antibody by antigens in the sample being assayed leads to a reduction in quenching and an increase in fluorescence. The extent of the inhibition of quenching is a measure of antigen concentration in the sample. In another preferred embodiment of an inhibition assay, the known antigen and antibody the original complex are bound to particles, for example, latex particles, of a size which permits agglomerates to form. When a sample suspected of containing antigen is contacted with the antibody and bound antigen, inhibition of agglomerate formation occurs because of complexing between the bound antibody and sample antigen which cannot form agglomerates. The reduction in agglomeration can be measured using turbidimetric techniques.

DETAILED DESCRIPTION OF THE INVENTION

As indicated above, according to the present invention, the polyclonal antibody used in an immunometric assay for an antigenic substance is replaced by a monoclonal antibody. Similarly, monoclonal antibodies are used in inhibition assays. The present invention is useful for the determination of the presence and concentration of a wide variety of antigenic substances including polyvalent antigenic substances. Accordingly, as used herein, the term antigen or antigenic substance refers broadly to substances to which antibodies can be produced. Among such substances may be mentioned haptens, hormones such as insulin and human thyroid stimulating hormone (HTSH), gamma globulins, allergens, viruses, virus subunits, bacteria, toxins such as those associated with tetanus and with animal venoms, and even some drugs. Among the specific antigens which may be assayed by the processes of the present invention may be mentioned carcinoembryonic antigen (CEA), hepatitis A and B, hepatitis Non A-Non B, IgE and alphafetoprotein.

The monoclonal antibodies useful in the present invention are obtained by the process discussed by Milstein and Kohler and reported in Nature 256 495-497, 1975. The details of this process are well known and will not be repeated here. However, basically it involves injecting a mouse, or other suitable animal, with an immunogen. The mouse is subsequently sacrificed and cells taken from its spleen are fused with myeloma cells. The results is a hybrid cell, referred to as a "hybridoma," that reproduces in vitro. The population of hybridomas is screened and manipulated so as to isolate individual clones each of which secretes a single antibody species to the antigen. Each individual antibody species obtained in this way is the product of a single B cell from the immune animal generated in response to a specific antigenic site recognized on the immunogenic substance.

When an immunogenic substance is introduced into a living host, the host's immune system responds by producing antibodies to all the recognizable sites on the substance. This "shotgun" approach to producing antibodies to combat the invader results in the production of antibodies of differing affinities and specificities for the immunogenic substance. Accordingly, after the different hybridoma cell lines are screened to identify those that produce antibody to the desired antigen, the antibodies produced by the individual hybridoma cell lines are preferably screened to identify those having the highest affinity for the immunogenic substance stimulating their original production before selection for use in the present invention. Selection based on this criterion is believed to help provide the increased sensitivity in the immunometric and inhibition assays of the present invention using monoclonal antibody compared to the polyclonal antibody used in the prior art which, at best, has an affinity for the antigen which is roughly the average of the affinities of all antibodies produced by the immune system. Preferably, the monoclonal antibody selected will have an affinity compatible with the desired sensitivity and range for the test system under consideration. Preferably the antibody will have an affinity of at least $10^8$ liters/mole and, more preferably, an affinity of at least about $10^9$ liters/mole.

Furthermore, those monoclonal antibodies having the highest affinities can be further screened by running a simulated assay on specimens known to give false positive results with processes employing conventional polyclonal antibodies to identify those monoclonal antibodies which do not cross-react and give false positive results.

Because the two-site immunometric assay relies upon formation of an antibody:antigen:antibody sandwich, usually two different monoclonal antibodies which do not interfere with the binding of each other to the antigen are selected to be the bound antibody and the soluble labelled antibody or the antibody pair when fluorescence quenching is used. Since both are necessary to complete the sandwich, reverse and simultaneous assays can be conducted without concern, for example, that a complex of labelled antibody:antigen:labelled antibody will form which will preclude formation of a complex between the antigen and the antibody bound to the solid phase and therein lies a particular advantage of the present invention. Furthermore, a forward assay can be accomplished without the intermediate washing step since the two antibodies bind to two different sites. We refer to such a process as a "fast forward" assay.

However, particularly in the case of a forward assay, the same monoclonal antibody can be used for both the labelled antibody and the antibody bound to the solid support when the antigenic substance possesses identical antibody binding sites sufficiently remote from each other to allow more than one antibody molecule to be bound at the same time. In such a system, the addition first of the bound antibody to the sample precludes formation of a sandwich because of steric considerations. When the labelled monoclonal antibody is subsequently added, it is also able to complex with the antigen bound to unlabelled antibody on the solid phase.

The unlabelled monoclonal antibody used in the process of the present invention to extract the antigenic substance from the sample being tested may be immobilized on any of the common supports used in immunometric assays. Among these may be mentioned filter paper, plastic beads or test tubes made from polyethylene, polystyrene, polypropylene or other suitable material. Also useful are particulate materials such as agarose, cross-linked dextran, and other polysaccharides. The techniques for bonding antibodies to such materials are well know to those skilled in the art. For example, antibodies may be bound to polysaccharide polymers using the process described in U.S. Pat. No. 3,645,852.

The labelled monoclonal antibody used in the present invention may be provided with the same labels used in prior art immunometric assays. Among these may be mentiond fluorogenic labels for detection by fluorimetry as described in U.S. Pat. No. 3,940,475 and enzymatic markers as described in U.S. Pat. No. 3,654,090. It is presently preferred to label the antibody with a radioisotope such as $^{125}I$ using, for example, the procedure of Hunter and Greenwood, *Nature*, 144 (1962), page 945 or that of David et al., Biochemistry, Vol. 13, pp. 1014–1021, 1974.

In a typical assay, the amount of labelled antibody associated with the insoluble sandwich complex is determined by examination of the insoluble carrier material by suitable means. However, it is also possible to relate the presence or absence of antigen in the fluid sample being assayed to the amount of labelled antibody which does not react during the assay and remains in soluble form.

The advantages of the present invention in which monoclonal antibodies are used in immunometric assays as compared to polyclonal antibodies are seen by reference to the following example. In this example, four comparative assays, a simultaneous assay, a reverse assay, a forward assay, and a "fast" forward assay, were run using both monoclonal antibody and polyclonal antibody using a standard serum containing 100 IU/ml of human IgE as the positive sample. Normal horse serum containing no IgE was used as a negative control.

The polyclonal antibody to IgE used as the labelled antibody in the example was obtained from Pharmacia Diagnostics of Piscataway, N.J. The polyclonal antibody bound to the solid support was obtained from Tago, Inc. of Burlingame, Calif.

Monoclonal antibody to IgE was obtained using the method of Milstein and Kohler discussed above. The two antibodies selected each exhibited an affinity for IgE of greater than $10^9$ liters/mole and did not interfere with the other's binding to IgE.

The assays were run using unlabelled antibody bound to agarose by the process of U.S. Pat. No. 3,645,852. Labelling of antibody was by $^{125}I$ according to the process of David et al. referred to above. Phosphate buffered saline, pH 7.4, was used to wash all samples.

EXAMPLE (1) Simultaneous Assay Method

Duplicate samples were run in which 100 µl of a suspension of antibody immobilized on agarose particles was mixed with 100 µl of specimen (serum) and 100 µl of soluble $^{125}I$-labelled antibody. This mixture was incubated for the specified times shown in Table I (for polyclonal antibody) and Table II (for monoclonal antibody) set forth below, plus 30 minutes. The extra 30 minutes incubation period was added to equalize this assay method with the other assay methods which required an additional 30 minutes incubation time for a second added reagent. Following the incubation periods the agarose particles were washed by addition of buffer and centrifuged. After removal of the washing liquid by aspiration, the resulting pellet of agarose particles was then counted for bound $^{125}I$-labelled antibody. The counts obtained for each of the complexes after the specified incubation time are set forth in Tables I and II.

(2) Reverse Assay Method

Duplicate samples were run in which 100 µl of specimen (serum) was mixed with 100 µl of $^{125}I$-labelled soluble antibody and incubated for the specified times shown in Tables I and II. 100 µl a suspension of antibody immobilized on agarose particles is then added and the mixture was allowed to incubate for another 30 minutes. The agarose particles were then washed and counted as in the simultaneous assay method. The counts are reported in Tables I and II.

(3) Forward Assay Method

Duplicate samples were run in which 100 µl of specimen (serum) was mixed with 100 µl of a suspension of antibody immobilized on agarose particles and incubated for the specified times shown in Tables I and II. The agarose particles were then washed once by the addition of 2.5–3.0 ml of buffer which, after mixing, was centrifuged, and the liquid removed by aspiration. 100 µl of $^{125}I$-labelled soluble antibody was then added and the mixture incubated an additional 30 minutes. The agarose particles were then washed and counted as in the simultaneous assay method. The counts are reported in Tables I and II.

(4) Fast Forward Assay Method

The assay was performed, in duplicate, in a similar manner to the forward assay method except that the wash step between the initial incubation of specimen with antibody immobilized on agarose particles and the addition of soluble $^{125}I$-labeled antibody was omitted.

Figure 1:
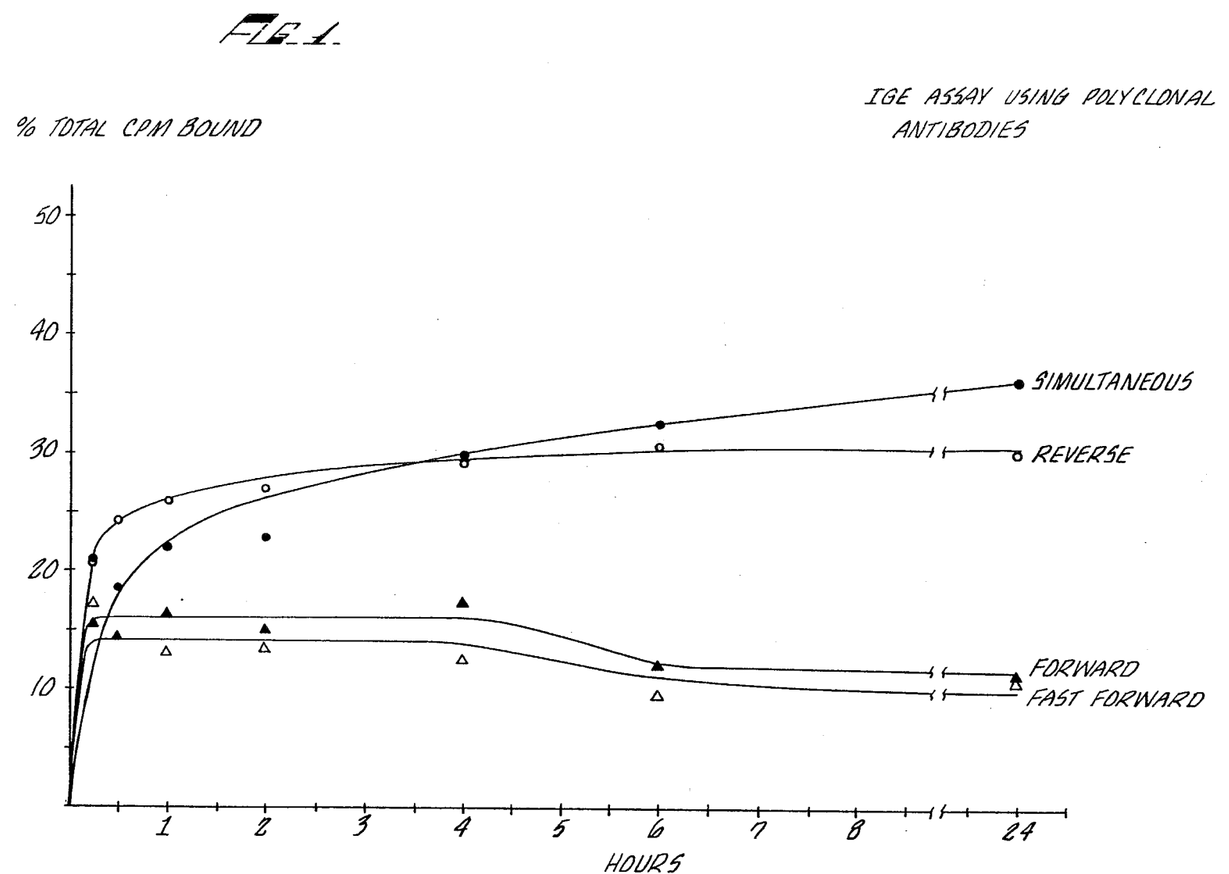
FIG. 1 is a graph illustrating the results obtained using polyclonal antibodies in four types of immunometric assay for human IgE.
Figure 2:
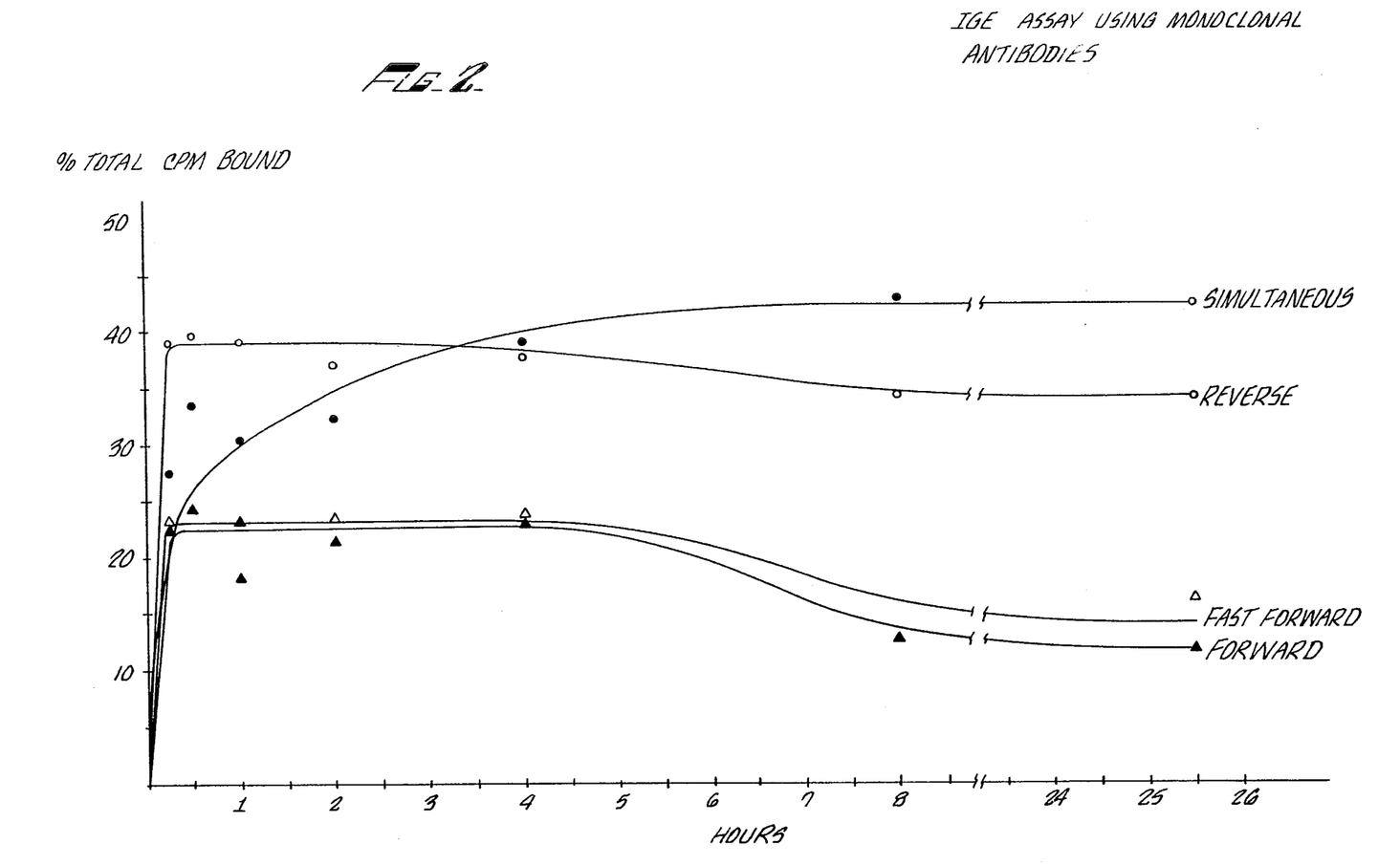
FIG. 2 is a similar graph illustrating the difference in results obtained using monoclonal antibodies in the same four types of immunometric assay for human IgE.

The counts/minute for the duplicate controls and the duplicate assays of the samples containing IgE using polyclonal antibody and monoclonal antibody are shown in Tables I and II, respectively. These data were used to prepare FIGS. I and II in the following way. The average of the counts/minute for a control for a given incubation period was subtracted from the average of the counts for the corresponding IgE assay. The difference was calculated as a percentage of the total counts/minute of labelled antibody added to the sample and is plotted on the Y axis as the percentage of total counts/minute of antibody bound to the solid phase. The incubation time is plotted on the X axis.

TABLE I

Assay Results Using Polyclonal Antibody

| Incubation Time (Hrs) | Simultaneous Assay | | Reverse Assay | | Forward Assay | | Fast Forward Assay | |
|---|---|---|---|---|---|---|---|---|
| | Control Samples | IgE Samples | Control Samples | IgE Samples | Control Samples | IgE Samples | Control Samples | IgE Samples |
| 0.25 | 372,314 | 2705,2667 | 302,243 | 2568,2581 | 357,326 | 2092,2077 | 396,293 | 2271,2238 |
| 0.50 | 348,265 | 2391,2366 | 284,262 | 2958,2999 | 288,233 | 1905,1817 | —,— | —,— |
| 1.00 | 315,277 | 2793,2708 | 305,277 | 3154,3218 | 355,424 | 2157,2255 | 304,284 | 1789,1706 |
| 2.00 | 342,356 | 2897,2887 | 290,274 | 3377,3212 | 302,314 | 1946,2019 | 288,312 | 1728,1867 |
| 4.00 | 421,385 | 3696,3746 | 28,280 | 3413,3651 | 274,255 | 2019,2392 | 283,292 | 1720,1683 |
| 6.00 | 447,436 | 4028,4101 | 296,281 | 3762,3643 | 241,267 | 1750,1452 | 301,257 | 1283,1424 |
| 24.00 | 526,577 | 4564,4628 | 233,263 | 3651,3546 | 320,277 | 1553,1604 | 273,256 | 1450,1470 |

TABLE II

Assay Results Using Monoclonal Antibody

| Incubation Time (Hrs) | Simultaneous Assay | | Reverse Assay | | Forward Assay | | Fast Forward Assay | |
|---|---|---|---|---|---|---|---|---|
| | Control Samples | IgE Samples | Control Samples | IgE Samples | Control Samples | IgE Samples | Control Samples | IgE Samples |
| 0.25 | 135,132 | 5610,5803 | 388,594 | 8407,8358 | 210,205 | 4618,4894 | 194,183 | 4859,4906 |
| 0.50 | 558,459 | 7472,7115 | 240,231 | 8238,8271 | 223,228 | 4987,5273 | 198,197 | 5024,5152 |
| 1.00 | 268,265 | 6289,6529 | 325,265 | 8010,8377 | 230,187 | 3454,4308 | 215,192 | 4887,4901 |
| 2.00 | 282,275 | 6787,6784 | 255,302 | 7856,7644 | 226,197 | 4834,4268 | 192,210 | 4937,4944 |
| 4.00 | 308,272 | 8150,8155 | 343,305 | 8017,7788 | 231,216 | 5269,4420 | 218,187 | 4929,5071 |
| 8.00 | 549,667 | 8884,9494 | 698,850 | 7870,7358 | 226,361 | 2006,3631 | 405,243 | 3033,3713 |
| 25.55 | 426,420 | 8669,9044 | 497,323 | 7037,7359 | 194,201 | 2465,2586 | 246,233 | 3945,2943 |

A comparison of the plots shown in FIG. 2 displaying the results of assays using monoclonal antibody with those of FIG. 1 of assays using using polyclonal antibody shows that in each kind of assay, simultaneous, reverse, forward, and fast forward, the assay using monoclonal antibody was more sensitive as indicated by the higher percentage of total counts bound to the solid phase with 100 IU IgE/ml specimen. Unexpectedly, in the case of the simultaneous and reverse assays, we have found that those run with monoclonal antibody reach equilibrium more rapidly than does the corresponding assay using polyclonal antibody. Therefore, by using a monoclonal antibody in these procedures, the time for the assay can be reduced significantly beyond the time saving achieved by merely eliminating a washing step. In that regard, the reverse assay with monoclonal antibody reached equilibrium in less than one hour. The same assay run with polyclonal assay did not reach equilibrium until after 4 hours. Similarly, in the case of simultaneous assays, the assay using monoclonal antibody reached equilibrium within 8 hours whereas the assay with polyclonal antibody did not reach equilibrium within 24 hours. Accordingly, the present invention provides substantially more rapid and sensitive simultaneous and reverse assays than the prior art processes and eliminates the concern that formation of a soluble "sandwich" complex will compete with formation of the desired insoluble complex.

In the foregoing discussion, the focus has been upon two site or sandwich assays in which one of the antibodies is insolubilized while the other is soluble in the medium analyzed. Other variations are possible. A preferred variant employs antibodies bound to particles, such as particles of latex, in a manner which results in each particle carrying a plurality of antibodies. When a quantity of particles to which a first monoclonal antibody is bound is admixed with, for example, quantity of particles to which a second monoclonal antibody is bound, a milky suspension results. However, if a sample containing polyvalent antigen for which the antibodies are specific is introduced to the suspension, agglomeration or agglutination of the particles will occur to form easily detectable particle clumps.

The visual detection of agglomerate formation can be used in a screening test for presence of the antigen. This detection can be aided by coloring the particles carrying one monoclonal antibody differently from the particle carrying the other. However, the extent of agglomeration can also be determined as a measure of the amount of antigen present in the sample. For example, the change in turbidity can be measured using standard techniques such as nephelometry.

It is presently preferred to use latex particles to which the antibody is covalently bound using techniques well known to those skilled in the art. However, other particulate supports can be used. Among these may be mentioned silica, glass, cells, polyacrylamides, polymethyl methacrylate and agarose. Preferably, the particles vary in size between about $0.2\mu$ to about $10\mu$. Visual screening, however, requires particles of at least about $10\mu$.

In yet another variant, one of the antibodies is insolubilized on a bead, test tube wall or other macroscopic solid support, and the other is bound to small particles of latex or other suitable material. In the presence of antigen, a sandwich of the antigen between the macroscopically bound antibody and the particle bound antibody will form. By, for example, coloring the particles, formation of the sandwich can be determined visually. A fluorescent, enzymatic, radioactive or other label on the particle bound antibody can be used for quantitative determinations just as in the case of using a soluble antibody described above.

In another preferred variant of the two-site assay, at least one of two different monoclonal antibodies is bound to an enzyme which catalyzes a reaction involving a substance bound to the other monoclonal antibody to produce either a detectable substance or in some other way interacts with the substance on the second antibody to permit detection of the antibody:antigen:antibody complex. Detection may be, for example, by colorimetry, fluorimetry, luminescence, spectrophotometry, or the like. It will be appreciated that, using such techniques, neither antibody needs to be insolubilized, greatly simplifying the assay.

In a presently preferred embodiment, the substance on the second antibody is also an enzyme and the assay employs the pair of enzyme labelled antibodies to catalyze sequential reactions, one of which produces a product required by the other. In those reactions, the two antibodies are selected so that when they bind with the antigen, they are sterically positioned so that the product of the first enzymatic reaction is generated in such close proximity to the second enzyme labelled antibody, that the second reaction occurs before significant diffusion of the product of the first reaction into the surrounding medium can take place.

This process can be illustrated using a pair of monoclonal antibodies, one of which is labelled with hexokinase (HK), the other with glucose-6-phosphate dehydrogenase (G-6-PDH), in the following series of reactions.

(1) adenosine triphosphate + glucose $\xrightarrow{HK}$
(ATP)
adenosine diphosphate + glucose-6-phosphate
(ADP)

(2) glucose-6-phosphate + nicotinamide adenine dinucleotide $\xrightarrow{G-6-PDH}$
(NAD$^+$)
gluconolactone-6-phosphate + dihydronicotinamide adenine dinucleotide
(NADH)

The assay is conducted by adding to the sample containing the suspect antigen the labelled antibodies to the antigen, ATP, glucose and the coenzyme NAD$^+$. If the antigen is present, a complex as illustrated below is formed:

The HK labelled antibody catalyzes the formation of glucose-6-phosphate in proximity to the G-6-PDH labelled antibody where it is converted to gluconolactone-6-phosphate. The NADH formed in this reaction by reduction of NAD$^+$ can be detected spectrophotometrically because of the strong absorption at 340 nm characteristic of a dihydronicotinamide.

The same conversion of glucose to gluconolactone-6-phosphate with formation of NADH also may occur in the medium itself catalyzed by the uncomplexed labelled antibodies, but at a much slower rate than when the two antibodies are positioned near each other in the antibody:antigen:antibody complex. Accordingly, an increase of absorption at 340 nm compared to a control sample confirms the presence of antigen in the sample. The increase in absorption can also be co-related to the quantity of antigen in the complex.

Any other pair of suitable sequential enzymatically catalyzed reactions may be used in a two-site assay with appropriately labelled antibodies to a suspect antigen. Among those may be mentioned the reaction of glucose catalyzed with glucose oxidase to form glucono-δ-lactone and hydrogen peroxide followed by the reaction of the hydrogen peroxide with o-phenylenediamine catalyzed by peroxidase to produce a colored moiety. In this assay, one of the monoclonal antibodies is labelled with glucose oxidase and the other with peroxidase. The intensity of the color produced compared to a control can be correlated to the presence and/or amount of antigen in the sample assayed. It will be appreciated that other substances oxidizable to a colored moiety in the presence of an enzyme can be substituted for o-phenylenediamine.

Yet another suitable pair of sequential reactions using a pair of antibodies to a desired antigen labelled, respectively, with NAD oxidoreductase and luciferase is the following:

(1) NADH + riboflavin-5'-phosphate $\xrightarrow{\text{NAD oxidoreductase}}$
(FMN)
FMNH$_2$ + NAD$^+$ (2) FMNH$_2$ + RCHO + O$_2$ $\xrightarrow{\text{luciferase}}$
FMN* + RCOOH + H$_2$O RCHO is typically a straight chain aldehyde of 10 or more carbon atoms. The generation of FMN*, an excited state of FMN, is followed by the emission of a photon which can be detected photometrically for correlation with a control sample to indicate the presence and/or quantity of antigen in a sample being assayed.

In another embodiment using a pair of antibodies labelled with enzymes, the product of the first enzymatically catalyzed reaction can be either an allosteric activator or inhibitor of the subsequent enzyme catalyzed reaction. An allosteric activator, rather than being consumed in the second reaction, interacts with the enzyme to increase its affinity for a substrate or to increase the rate of conversion of the substrate to product after the enzyme-substrate complex is formed. Allosteric inhibitors, on the other hand, have the opposite effect and reduce the enzyme's affinity for a substrate or reduce the rate of conversion of substrate to product. Allosteric inhibition may be of the competitive or noncompetitive type.

An example of an assay involving allosteric activation employing a pair of antibodies labelled, respectively, with phosphofructokinase and phosphoenolpyruvate uses the following reaction scheme:

(1) fructose-6-phosphate + ATP $\xrightarrow{\text{phosphofructokinase}}$
fructose-1,6-diphosphate + ADP (2) HCO$_3^-$ + phosphoenolpyruvate $\xrightarrow{\text{phosphoenolpyruvate carboxylase}}$
(PEP)
oxaloacetate
(OAA)

-continued (3) OAA + NADH  malate + NAD$^+$

The fructose-1,6-diphosphate formed in reaction (1) allosterically interacts with the phosphoenolpyruvate carboxylase and activates its catalysis of reaction (2), the formation of oxaloacetate from PEP. Reaction (3) occurs in the surrounding medium, i.e., there is no necessity to bind the malate dehydrogenase to a third monoclonal antibody. The presence and/or quantity of suspect antigen is determined by correlating the reduction in the absorption at 340 nm by NADH which is oxidized in reaction (3) to NAD$^+$.

An example of an assay involving allosteric inhibition employing a pair of antibodies labelled, respectfully, with aspartate amino transferase (AST) and phosphoenolpyruvate carboxylase can use the following reaction scheme:

(1) oxaloocetate + glutamate $\xrightarrow{AST}$ aspartate + α-ketoglutorate (2) PEP + NADH $\xrightarrow{\text{phosphoenolpyruvate carboxylase}}$ OAA + NAD$^+$

The aspartate formed in reaction (1) inhibits the second reaction by allosterically interacting with the phosphoenolpyruvate carboxylase. This reduces the rate at which NADH is oxidized to NAD$^+$. Therefore, the decrease in the absorption at 340 nm exhibited by NADH can be correlated to the presence and/or quantity of antigen in the sample being assayed, a smaller decrease than occurs with a control sample indicating that antigen is present.

Those skilled in the art will appreciate that numerous other reaction pairs involving activation or inhibition of the second enzymatically catalyzed reaction can be substituted for the examples set forth above for use in a two-site assay. In another embodiment, only one of the antibody pairs is labelled with an enzyme, the second being labelled with a substance, for example, that undergoes a reaction catalyzed by the enzyme to produce a second product which can be detected and/or quantified by colorimetric, fluorimetric, luminescence, spectrophotometric or other technique. One such example uses a pair of monoclonal antibodies, one of which is labelled with peroxidase and the other with luminol, and takes advantage of the following reaction:

luminol

-continued $N_2 + 2H_2O + h\nu +$

The photon (h$\nu$) emitted by the reaction can be detected using photometric techniques and related to the presence and/or quantity of an antigen in a sample being assayed.

In yet another preferred variant of the two-site assay, the two monoclonal antibodies are, respectively, conjugated with a fluorescing chromophore and a quenching chromophore which absorbs light at the wavelength emitted by the fluorescer. The two antibodies are selected so that, when they combine with the antigen for which they are specific, the two chromophores are positioned close enough to permit the light emitted by the fluorescer to be absorbed by the other chromophore. Usually, this will place them within about 100 angstroms of each other and, preferably, within about 50 angstroms of each other. The selection of suitable antibodies can be done through a screening procedure in which a mixture of fluorescent and quencher labelled monoclonal antibodies are contacted with a sample containing a known quantity of antigen. Reduction of fluorescence is indicative that the two chromophores are positioned closely enough together.

Using fluorescence quenching, it is unnecessary to insolubilize either of the two antibodies. Quantitative measurements can be made simply by measuring the decrease in maximum fluorescence, i.e., the amount of fluorescense exhibited by a control sample free of any antigen or by comparing the fluorescence of the sample with that of control samples containing a known quantity of antigen. However, fluorescent-quenching chromophore pairs can also be used in combination with the particle agglomeration technique and in the technique whereby one of the antibodies is insolubilized by being bound to a solid support such as a test tube wall or bead, since pairing of the fluorescent-quenching chromophores will occur. A decrease in fluorescence again is indicative of the presence or amount of antigen in the sample.

Suitable fluorescing and quenching chromophores and techniques for conjugating them with antibodies are described in U.S. Pat. No. 4,174,384, the disclosure of which is incorporated by reference. Presently, it is preferred to use fluorescein and rhodamine as the flurorescer and quencher chromophores, respectively.

In the preceding discussion of our invention, we have described techniques of fluorescence quenching in which antibody pairs carrying the necessary chromophores are caused to bond to an antigen, if present in the sample being analyzed, in a steric arrangement which permits the quenching chromophore to absorb light emitted by the fluorescent chromophore. Quantitative determinations of the amount of antigen present are made by measuring the decrease in maximum fluorescence.

These techniques are well suited to determining the presence of antigen in a sample over a wide range of concentration. However, the small decreases in fluorescence which are associated with low antigen concentration are hard to detect and measure accurately. By contrast, small increases in fluorescence are relatively easy to detect and measure accurately. Accordingly, in another aspect of our invention, we prefer to exploit the inhibition of quenching and measure increases in fluorescence.

To accomplish this in an assay for a particular antigen, quantities of the antigen and monoclonal antibody to the antigen are individually labelled with one or the other of the pair of fluorescent-quencher chromophores. The chromophore labelled antigen and antibody are then combined to form a complex in which the fluorescent chromophore is positioned so that the light it emits is absorbed by the quenching chromophore. to achieve this the antigen may be labelled with the fluorescer and the antibody with the quencher or vice versa.

A sample suspected of containing the antigen being assayed is then contacted with the chromophore labelled antigen and antibody. After a suitable incubation period, fluorescence is measured. If antigen is present in the assayed sample, it inhibits, at least in part, the formation of a complex between the chromophore labelled antigen and the antibody by itself forming a complex with the monoclonal antibody. To the extent this occurs, the fluorescer chromophore is no longer positioned so that the light it emits is absorbed by the quenching chromophore. This results in an increase in fluorescence. The increase in fluorescence can be measured and related to the concentration of antigen in the sample undergoing analysis by comparison with the fluorescence exhibited by control samples free of antigen or containing known amounts of antigen.

From the foregoing, it will be apparent that the chromophore labelled antigen:antibody complex may be a soluble one. However, it is presently preferred to employ chromophore labelled antigen and monoclonal antibody which are bound to latex or other suitable particles, for example, those listed above, of a size that will form agglomerates when the complex is formed. Particles varying in size from about 0.2 to about $10\mu$ are usually suitable for this purpose. When an unknown sample containing the suspect antigen is contacted with the agglomerate forming particles of antibody and antigen, inhibition of agglomeration will occur because of sample antigen combining with particle-bound antibody. An increase in fluorescence will result, since quenching can no longer occur, which can be detected and measured to correlate with the amount of antigen in the sample by comparison with the fluoresence observed for a sample containing a known quantity of antigen.

It is also within the scope of our invention to employ bound antigen and particle bound monoclonal antibody in an assay that directly measures the inhibition of agglomeration. In this technique, neither the antigen nor antibody is labelled. When a sample containing antigen is contacted with the particles, inhibition of agglomeration during the incubation period will occur. This results in, at least, a partial reduction in the agglomerate formation. The inhibition is detected using nephelometry or other techniques for measuring turbidity. The decrease in turbidity can be correlated to the amount of antigen in the sample.

The foregoing description of the invention and the examples demonstrating the application of the invention to assays for IgE are but exemplary of the various ways the invention can be utilized. That other variations will be useful will be apparent to those skilled in the art.

Therefore, the present invention is to be considered limited only by the appended claims.

We claim:

1. In an immunometric assay process to determine the presence or concentration of an antigenic substance in a fluid sample comprising forming a ternary complex of the antigenic substance, a first antibody and a second antibody bound to the antigen at a difference site than the first antibody by contacting the sample with said first and second antibodies, the improvement comprising employing a measured amount of a monoclonal antibody having an affinity for the antigenic substance of at least about $10^8$ liters/mole for each of said first and second antibodies.

2. A process according to claim 1 wherein a fluorescent chromophore is bonded to said first antibody and a chromophore capable of absorbing light at the wavelength emitted by the fluorescent chromophore is bonded to said second antibody, the monoclonal antibodies being capable of binding to the antigenic substance at sites which permit the light emitted by the fluorescing chromophore to be absorbed by the quenching chromophore.

3. A process according to claim 2 wherein the sample is contacted with a solution containing the first and second antibodies to form the ternary complex and the intensity of fluorescence determined and compared to the fluorescence of a standard sample free of said antigen or containing said antigen in a known amount.

4. A process according to claim 2 wherein the first antibody is bound to a solid carrier that is insoluble in the fluid sample and said second antibody is soluble in the fluid sample.

5. A process according to claim 4 wherein the fluid sample is simultaneously contacted with said first and second antibodies to form an insoluble ternary complex and the intensity of fluorescence of the ternary complex determined and compared to the fluorescence of a standard sample free of said antigen or containing said antigen in a known amount.

6. A process according to claim 2 wherein the second antibody is bound to a solid carrier that is insoluble in the fluid sample and said first antibody is soluble in the fluid sample.

7. A process according to claim 6 wherein the fluid sample is simultaneously contacted with said first and second antibodies to form an insoluble complex and the intensity of fluorescence of the fluid determined and compared to the fluorescence of a standard sample free of said antigen or containing said antigen in a known amount.

8. A process according to claims 4 or 6 wherein the sample is first contacted with the first antibody to form an antibody:antigen binary complex and then contacted with the second antibody to form the ternary complex and the intensity of the fluorescence of the complex or the fluid determined and compared to a standard sample free of said antigen or containing the antigen in a known amount.

9. A process according to claims 2, 3, 4, 5, 6, or 7 wherein the fluorescent chromophore is fluorescein and the chromophore capable of absorbing emitted light is rhodamine.

10. A process according to claim 8 wherein the fluorescent chromophore is fluorescein and the chromophore capable ot absorbing emitted light is rhodamine.

11. A process according to claim 1 wherein said first antibody is bound to particles insoluble in the fluid sample and said second antibody is bound to particles insoluble in the fluid sample and wherein the sample is contacted with a suspension of the particles for a time sufficient to cause formation of the ternary complex whereby agglomeration of the particles bound to said first and second antibodies occurs.

12. A process according to claim 11 wherein the size of the particles is in the range of from about 0.2μ to about 10μ.

13. A process according to claim 12 wherein the particles are selected from the group consisting of particles of latex, silica, glass, cells, polyacrylamide, polymethyl methacrylate and agarose.

14. A process according to claim 13 wherein the particles are latex particles.

15. A process according to claims 11, 12, 13, or 14 wherein the particles binding the first antibody are of different color than the particles binding the second antibody.

16. A process according to claims 12, 13, or 14 wherein the size of the particles is in the range of from about 1.0 to 10μ.

17. A process according to claim 15 wherein the size of the particles is in the range of from about 1.0 to 10μ.

18. A process according to claims 11, 12, 13, or 14 wherein the turbidity of the sample after formation of the ternary complex is determined and related to the turbidity of a control sample known to be free of the antigen or to contain a known amount of the antigen.

19. A process according to claims 11, 12, 13, or 14 wherein a fluorescent chromophore is bound to said first antibody and a chromophore capable of absorbing light at the wavelength emitted by the fluorescent chromopore is bound to the second antibody and wherein, after said contacting, the intensity of fluorescence is determined and compared to the fluorescence of a standard sample free of said antigen or containing said antigen in a known amount.

20. A process according to claim 19 wherein the fluorescent chromophore is flurescein and the chromophore capable of absorbing emitted light is rhodamine.

21. A process according to claim 1 wherein an enzyme is bound to the first antibody and a substance is bound to the second antibody whereby the enzyme interacts with the substance to permit detection of the antibody:antigen:antibody complex.

22. A process according to claim 21 wherein the substance bound to the second antibody is an enzyme.

23. A process according to claim 22 whereby the first antibody bound enzyme catalyzes a reaction which produces a product required by a reaction catalyzed by the second antibody bound enzyme.

24. A process according to claim 23 whereby the product of the reaction catalyzed by the first bound enzyme is consumed in the reaction catalyzed by the second bound enzyme.

25. A process according to claim 23 whereby the product of the reaction catalyzed by the first bound enzyme allosterically interacts with the second bound enzyme.

26. A process according to claim 25 whereby the product of the reaction catalyzed by the first bound enzyme allosterically activates the second bound enzyme.

27. A process according to claim 25 whereby the product of the reaction catalyzed by the first bound enzyme allosterically inhibits the second bound enzyme.

28. A process according to claims 23, 24, 25, 26 or 27 wherein the reaction catalyzed by the second antibody bound enzyme produces a detectable product.

29. A process according to claim 28 wherein the formation of the detectable product is detected by colorimetry, fluorimetry, luminescence or spectrophotometry.

30. A process according to claims 23, 24, 25, 26 or 27 wherein the reaction catalyzed by the second antibody bound enzyme consumes a detectable substance.

31. A process according to claim 30 wherein the consumption of the detectable substance is detected by colorimetry, fluorimetry, luminescence or spectrophotometry.

32. A process according to claim 21 wherein the substance on the second antibody undergoes a reaction catalyzed by the first antibody bound enzyme.

33. A process according to claim 32 wherein the reaction produces a substance detectable by colorimetry, fluorimetry, luminescence or spectrophotometry.

* * * * *

UNITED STATES PATENT AND TRADEMARK OFFICE
CERTIFICATE OF CORRECTION

PATENT NO. : 4,486,530
DATED : December 4, 1984
INVENTOR(S) : Gary S. David et al.

It is certified that error appears in the above-indentified patent and that said Letters Patent is hereby corrected as shown below:

On the title page: [*] Notice should read "Mar. 8, 2000" should read --August 4, 2000--.

Signed and Sealed this

Ninth Day of November, 1999

Attest:

Attesting Officer

Q. TODD DICKINSON

Acting Commissioner of Patents and Trademarks